US012778808B2

(12) United States Patent
Yang

(10) Patent No.: US 12,778,808 B2
(45) Date of Patent: Nov. 3, 2026

(54) HOW TO MOLD DIFFERENT TYPES OF MEDICAL PATCHES IN ONE PROCESS LINE

(71) Applicant: LTY CO., Ltd, Hwaseong-si (KR)

(72) Inventor: Gyeongmo Yang, Hwaseong-si (KR)

(73) Assignee: LTY CO., Ltd, Hwaseong-si (KR)

( * ) Notice: Subject to any disclaimer, the term of this patent is extended or adjusted under 35 U.S.C. 154(b) by 45 days.

(21) Appl. No.: 18/984,859

(22) Filed: Dec. 17, 2024

(65) Prior Publication Data

US 2025/0213396 A1 Jul. 3, 2025

(30) Foreign Application Priority Data

Dec. 28, 2023 (KR) ........................ 10-2023-0195511

(51) Int. Cl.
*A61F 13/02* (2024.01)

(52) U.S. Cl.
CPC ................................ *A61F 13/0289* (2013.01)

(58) Field of Classification Search
CPC ............................. A61F 13/02; A61F 13/0289
See application file for complete search history.

(56) References Cited

U.S. PATENT DOCUMENTS 4,951,444 A * 8/1990 Epstein .................. B29C 51/46 53/64

FOREIGN PATENT DOCUMENTS

| | | | | | |
|---|---|---|---|---|---|
| DE | 102004016591 | A1 * | 10/2005 | ........... | A61K 9/7053 |
| JP | 2001195585 | A * | 7/2001 | | |
| JP | 4891567 | B2 * | 3/2012 | | |
| KR | 10-1248121 | B1 | 4/2013 | | |
| KR | 10-1313495 | B1 | 10/2013 | | |
| KR | 10-2015-0134030 | A | 12/2015 | | |
| KR | 10-1842697 | B1 | 3/2018 | | |
| KR | 101934430 | B1 * | 1/2019 | ............ | B65B 35/56 |

OTHER PUBLICATIONS

Machine translation JP2001195585A (Year: 2001).*
Machine translation DE102004016591A1 (Year: 2005).*
Machine translation JP4891567B2 (Year: 2012).*
Machine translation KR101842697B1 (Year: 2018).*
Machine translation KR101934430B1 (Year: 2019).*
https://www.thefreedictionary.com/blankingThe Free Dictionary by Farley (Year: 2020).*
Machine translation KR101313495B1 (Year: 2013).*
Machine translation KR101248121B1 (Year: 2013).*
Machine translation KR1020150134030A (Year: 2013).*

* cited by examiner

*Primary Examiner* — Abbas Rashid
*Assistant Examiner* — Wayne K. Swier
(74) *Attorney, Agent, or Firm* — Revolution IP, PLLC

(57) ABSTRACT

The present invention provides a method for molding medical patches using a medical patch molding apparatus including: a first process, which is an eye-mark recognition process for recognizing eye marks formed on the surface of a fabric sheet; a second process, which is a beveling process of compressing and thinning edges of a patch; and a third process, which is a complete cutting process of blanking a release sheet to form a handle part, wherein any one among the first to third processes is applied depending on the type of the patch, allowing different types of medical patches to be molded in a single process line.

3 Claims, 4 Drawing Sheets

HOW TO MOLD DIFFERENT TYPES OF MEDICAL PATCHES IN ONE PROCESS LINE

CROSS-REFERENCE TO RELATED APPLICATIONS

This application claims priority to and the benefit of Korean Patent Application No. 10-2023-0195511 filed on Dec. 28, 2023, the disclosures of which is incorporated herein by reference in its entirety.

BACKGROUND OF THE INVENTION

The present invention relates to a method for molding different types of medical patches in a single process line, and more specifically to, a method for molding medical patches, which can mold and package medical dressing patches of various sizes using a single piece of equipment.

In general, dressing patches are widely used to protect and treat skin wounds such as minor burns, cuts, and injuries. The dressing patches function to prevent further contamination by reducing heat evaporation and moisture loss from the wound surface and provide the function of reducing bacterial growth within the wound. Such medical dressing patches are configured with an adhesive sheet attached to the upper surface of a release sheet. When a user separates the adhesive sheet from the release sheet and attaches the adhesive surface formed on the bottom surface of the adhesive sheet to the wound area, the dressing patches show the aforementioned functions.

As conventional technologies related to equipment for molding such medical dressing patches, Patent Document 1 discloses a molding and packaging apparatus for wound-protecting dressing materials, Patent Document 2 discloses a molding and packaging apparatus for wound-protecting dressing materials, Patent Document 3 discloses an apparatus and a method for manufacturing medical dressing materials, and Patent Document 4 discloses a manufacturing method for medical dressing bands.

However, the conventional dressing material molding apparatuses perform processes for molding different types of dressing materials with different sizes and shapes in a single device or perform the processes while replacing different molds, so require considerable time for operation and consume a significant amount of dressing fabric wasted until the setup is complete. Additionally, due to the sticky nature of the dressing fabric, the conventional dressing material molding apparatuses are highly likely to cause defects during processes such as transport, molding, insertion, attachment of the backing sheet, and retrieval of residual materials, resulting in decreased productivity.

Additionally, as various characters are increasingly printed on the surface of the fabric sheet, half-cutting or molding must be performed precisely at a correct position. However, if the fabric sheet is deformed or twisted, half-cutting or molding cannot be performed at the position of the character, leading to defects.

PATENT LITERATURE

Patent Document 1: Korean Patent No. 10-1248121 (granted on Mar. 21, 2013)

Patent Document 2: Korean Patent No. 10-1313495 (granted on Sep. 24, 2013)

Patent Document 3: Korean Patent No. 10-1842697 (granted on Mar. 21, 2018)

Patent Document 4: Korean Patent Publication No. 10-2015-0134030 (published on Dec. 1, 2015)

SUMMARY OF THE INVENTION

Accordingly, the present invention has been made to solve the above-mentioned problems occurring in the prior arts, and it is an objective of the present invention to provide a method for molding medical patches, which can mold and package medical dressing patches of various sizes using a single piece of equipment by sequentially arranging a plurality of processes in a single line.

It is another objective of the present invention to provide a process in which half-cutting or molding can be accurately performed at the correct position on a fabric sheet on which a character is printed.

The objectives of the present disclosure are not limited to those mentioned above, and other objectives not mentioned herein will be clearly understood by those skilled in the art from the following description.

To accomplish the above objectives, according to the present invention, there is provided a method for molding medical patches using a medical patch molding apparatus including: a first process, which is an eye-mark recognition process for recognizing eye marks formed on the surface of a fabric sheet; a second process, which is a beveling process of compressing and thinning edges of a patch; and a third process, which is a complete cutting process of blanking a release sheet to form a handle part, wherein any one among the first to third processes is applied depending on the type of the patch, allowing different types of medical patches to be molded in a single process line.

Moreover, the first process, the second process, and the third process are sequentially arranged in the single process line. After supplying the medical patch fabric sheet to the sequentially arranged single process line, the patch fabric sheet passes through the first to third processes in sequence. One of the first to third processes is selectively performed depending on the type of the patch to complete the patch.

Furthermore, the single process line includes: a fabric sheet supply unit, which supplies a fabric sheet on which a release sheet is adhered while unrolling the fabric sheet; an eye-mark recognition unit, which recognizes eye marks formed on the surface of the fabric sheet; a molding unit, which heats, presses and molds the fabric sheet into a predetermined shape using a press mold having a built-in heater; a cooling unit, which cools the fabric sheet molded in the molding unit; a fabric sheet half-cutting unit, which forms half-cut grooves along the outer boundary of a molded part of the fabric sheet in a cooled state by the cooling unit; a fabric sheet retrieval unit, which retrieves remaining fabric sheet except for patch fabric cut by the fabric sheet half-cutting unit; a release sheet complete-cutting unit, which forms grooves along the outer boundary of a handle part on the surface of the release sheet exposed by the fabric sheet retrieval unit; a protective film supply unit, which supplies a protective film; a protective film half-cutting unit, which removes edges of the protective film; and a protective film retrieval unit, which retrieves remaining protective film except for the protective film cut by the protective film half-cutting unit, wherein the eye-mark recognition unit which recognizes the eye marks formed on the surface of the fabric sheet corresponds to the first process, the molding unit and the cooling unit correspond to the second process, and the release sheet complete-cutting unit corresponds to the third process.

Additionally, depending on the selective operation of the first process, the second process, and the third process, the results of the first process are divided into first-process non-performed products and first-process performed products, the results of the second process are divided into second-process non-performed products and second-process performed products, and the results of the third process are divided into third-process non-performed products and third-process performed products, wherein according to the paths of the first to third processes, a total of eight types of patches can be produced in the single process line.

In addition, the types of the patches produced in the single process line are one of: a first patch manufactured without performing the eye-mark recognition unit, without performing the molding unit and the cooling unit, and without performing the release sheet complete-cutting unit; a second patch manufactured without performing the eye-mark recognition unit, without performing the molding unit and the cooling unit, but by performing the release sheet complete-cutting unit; a third patch manufactured without performing the eye-mark recognition unit, by performing the molding unit and the cooling unit, and without performing the release sheet complete-cutting unit; a fourth patch manufactured without performing the eye-mark recognition unit, by performing the molding unit and the cooling unit, and by performing the release sheet complete-cutting unit; a fifth patch manufactured by performing the eye-mark recognition unit, without performing the molding unit and the cooling unit, and without performing the release sheet complete-cutting unit; a sixth patch manufactured by performing the eye-mark recognition unit, without performing the molding unit and the cooling unit, and by performing the release sheet complete-cutting unit; a seventh patch manufactured by performing the eye-mark recognition unit, by performing the molding unit and the cooling unit, and without performing the release sheet complete-cutting unit; and an eighth patch manufactured by performing the eye-mark recognition unit, by performing the molding unit and the cooling unit, and by performing the release sheet complete-cutting unit.

The above and other features and advantages of the present invention will be more clearly understood from the following detailed description taken in conjunction with the accompanying drawings.

The terms and words used in the specification and claims must not be limited to typical or dictionary meanings, but must be regarded as concepts selected by the inventor as concepts which best illustrate the present invention, and must be interpreted as having meanings and concepts adapted to the scope and spirit of the present invention to aid in understanding the technology of the present invention.

As described above, according to the present invention, various sizes of dressing patches can be molded and packaged in a single piece of equipment, and a total of eight types of patches can be produced in a single process line according to paths of first to third processes.

DETAILED DESCRIPTION OF THE PREFERRED EMBODIMENT

Figure 1:
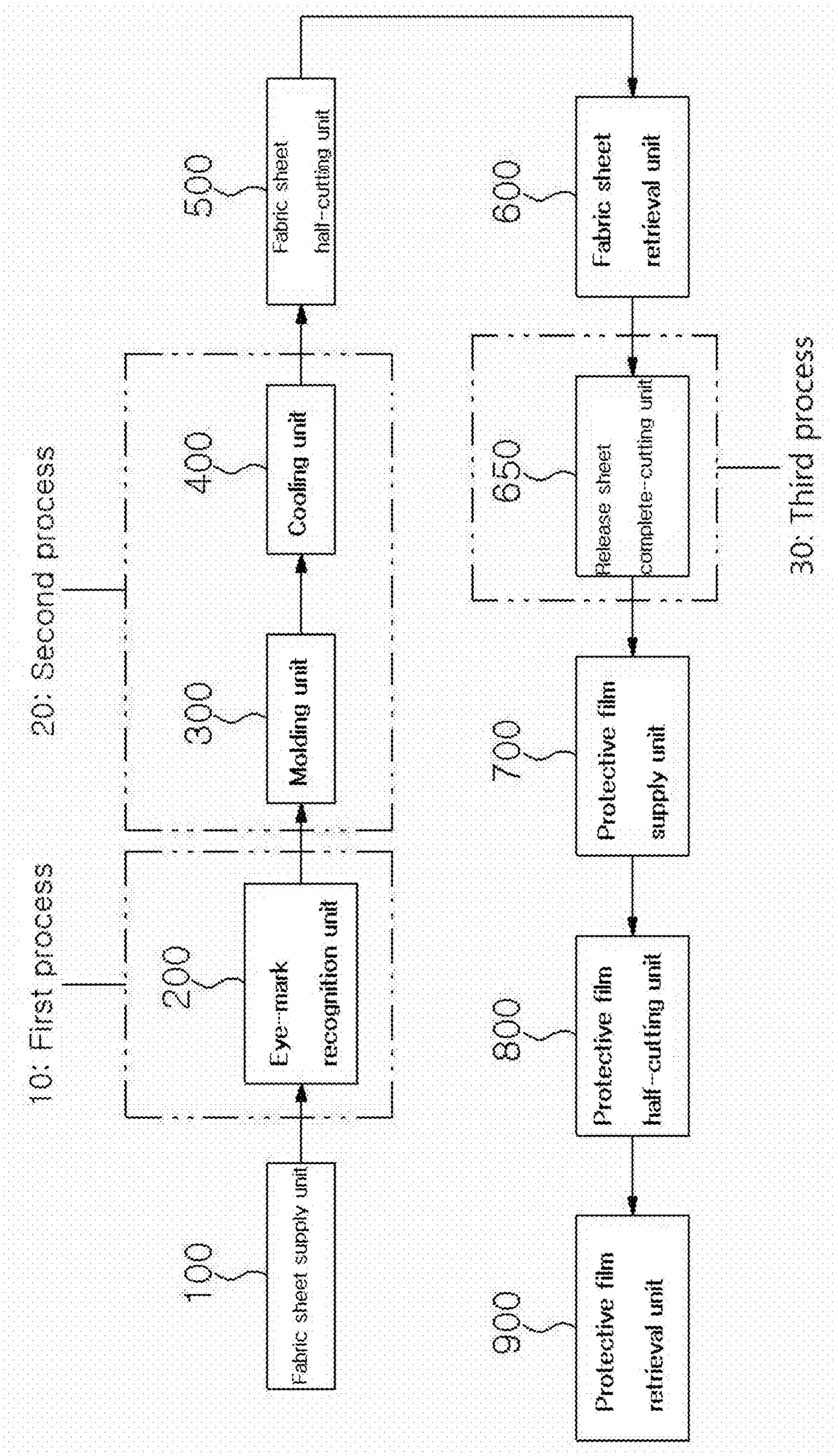
FIG. 1 is a block diagram listing a single process line according to a preferred embodiment of the present invention.

Hereinafter, exemplary embodiments of the present invention will be described with reference to the accompanying drawings. In the drawings, thicknesses of lines and sizes of constituent elements may be exaggerated for clarity and convenience in explanation.

Furthermore, words or terms to be described later are defined in consideration of the functions of the present invention, and may differ depending on the intentions of a user or an operator or custom. Accordingly, such wordings should be defined on the basis of the contents of the overall specification.

In addition, the embodiment disclosed hereinafter does not limit the scope of the present invention, but corresponds to merely exemplary terms of constituent elements presented in claims of the present invention, and the embodiments that include replaceable constituent elements as equivalents of the constituent elements defined in the overall specification and claims may be included in the scope of the present invention.

Figure 2:
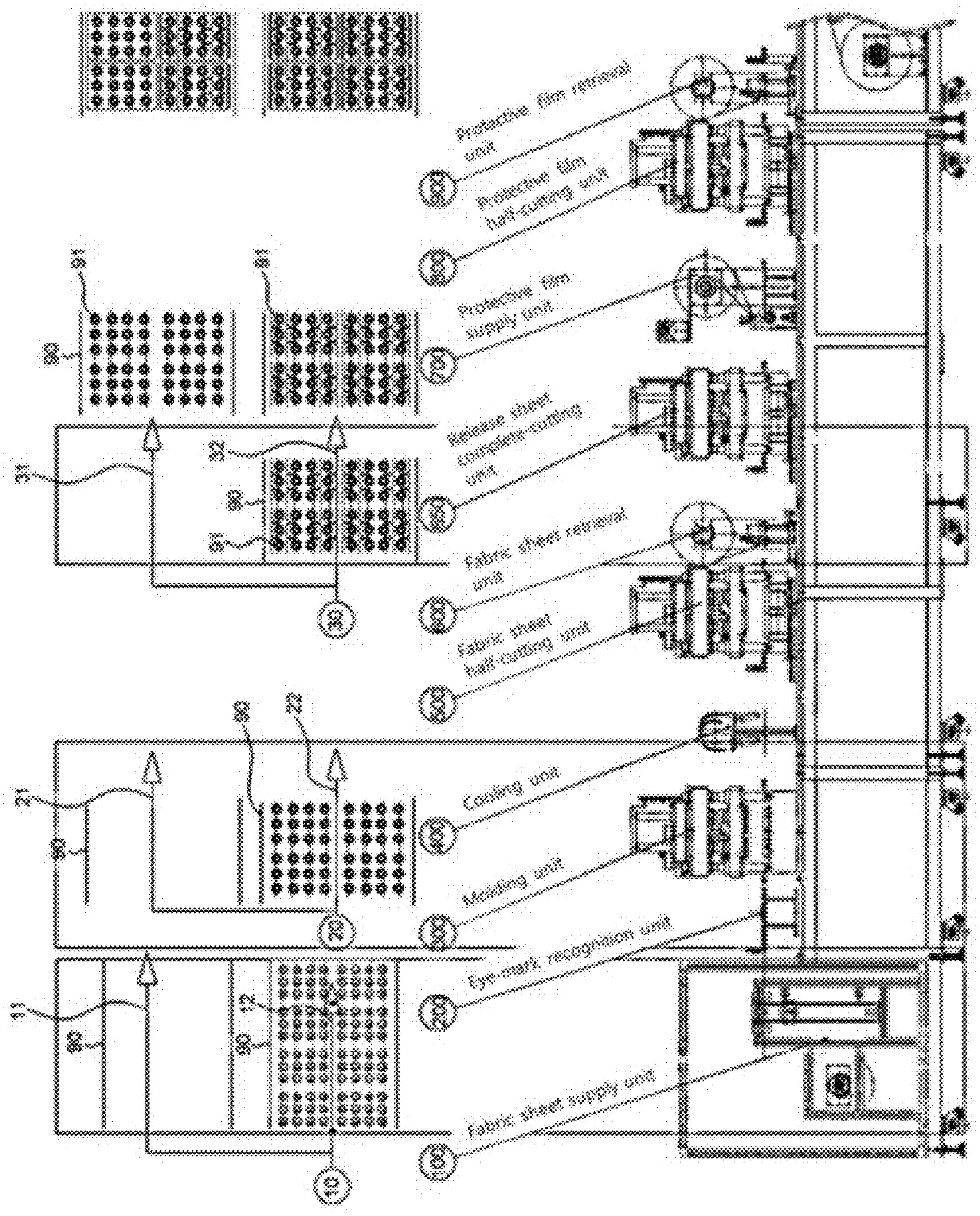
FIG. 2 is a front view illustrating the entire configuration of a packaging apparatus according to a preferred embodiment of the present invention and a schematic view illustrating fabric conditions according to the process line.
Figure 3:
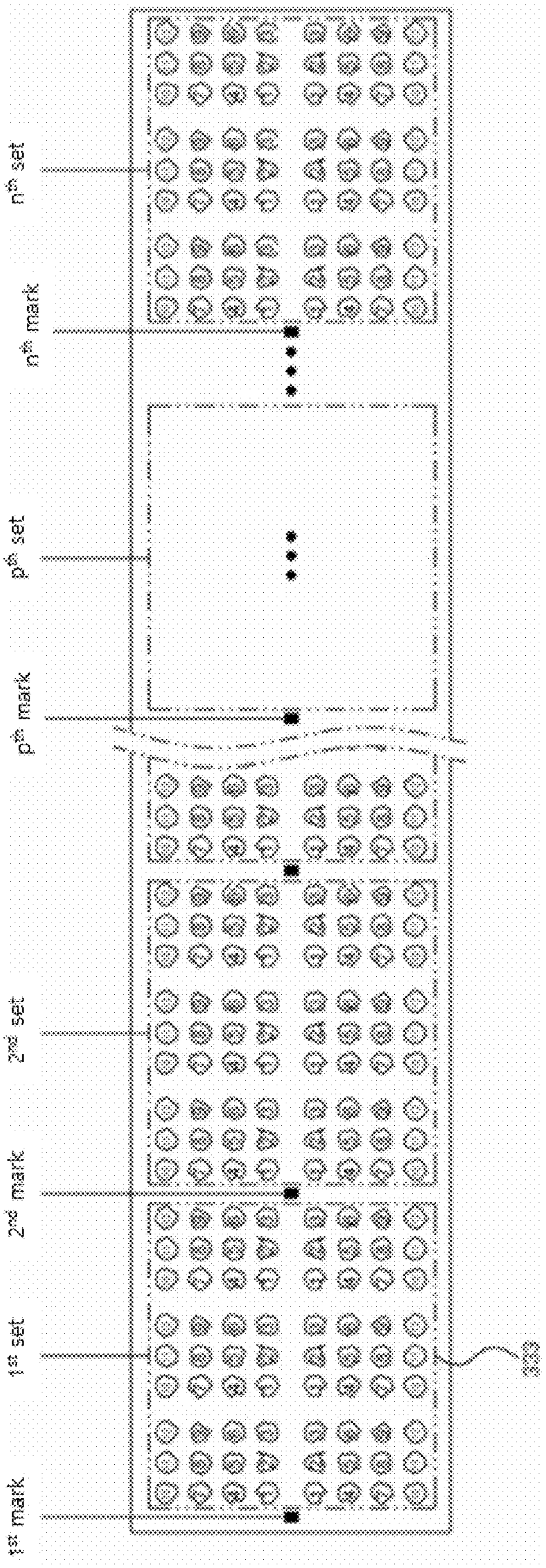
FIG. 3 is a schematic view illustrating a fabric sheet with eye marks and a plurality of characters printed thereon according to a preferred embodiment of the present invention.
Figure 4:
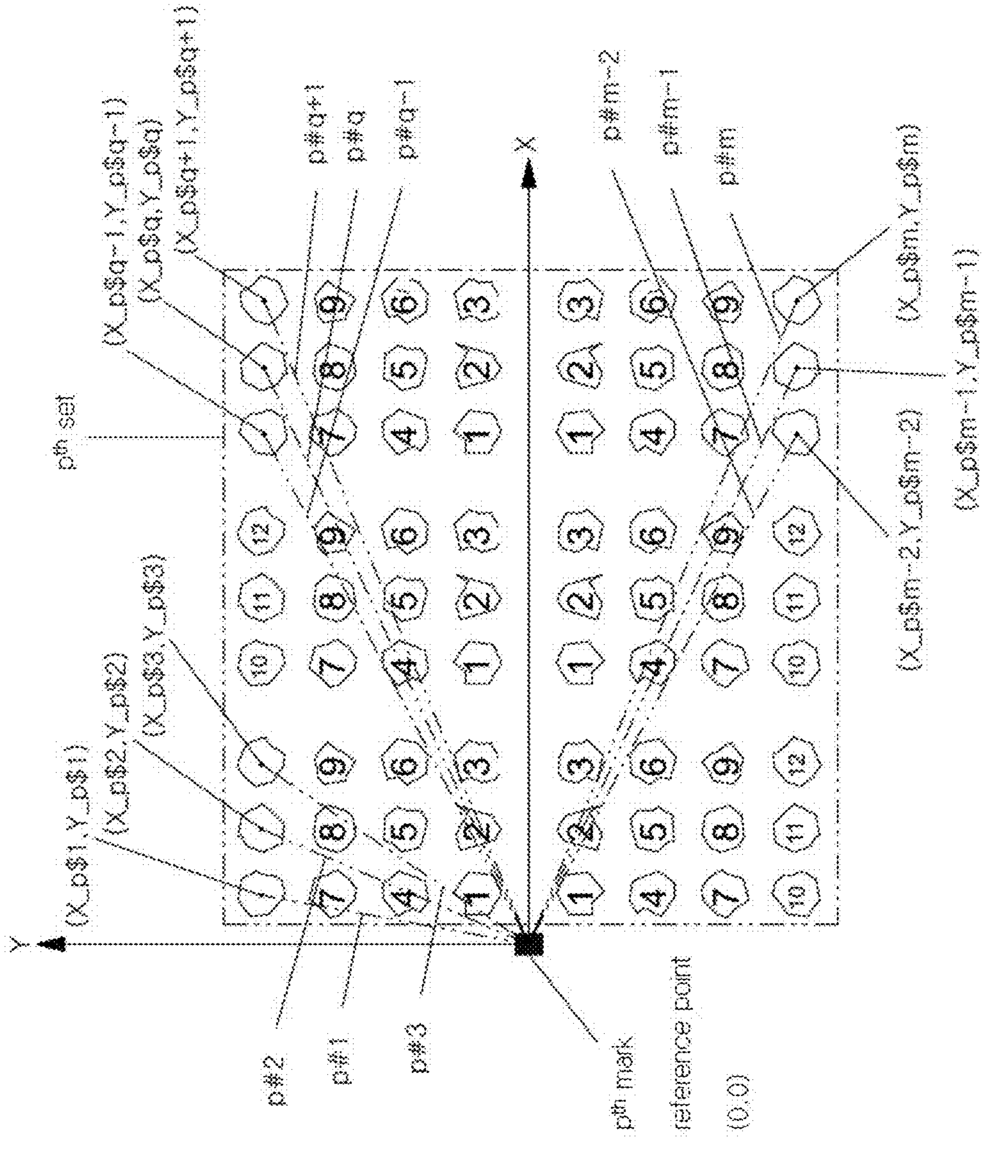
FIG. 4 is a schematic view illustrating the coordinate values of printed characters in p marks and p sets according to a preferred embodiment of the present invention.

FIG. 1 is a block diagram listing a single process line according to a preferred embodiment of the present invention, FIG. 2 is a front view illustrating the entire configuration of a packaging apparatus according to a preferred embodiment of the present invention and a schematic view illustrating fabric conditions according to the process line, FIG. 3 is a schematic view illustrating a fabric sheet with eye marks and a plurality of characters printed thereon according to a preferred embodiment of the present invention, and FIG. 4 is a schematic view illustrating the coordinate values of printed characters in p marks and p sets according to a preferred embodiment of the present invention.

As illustrated in FIG. 1 and subsequent drawings, a method for molding medical patches using a medical patch molding apparatus according to the present invention includes: a first process 10, which is an eye-mark recognition process for recognizing eye marks formed on the surface of a fabric sheet 90; a second process 20, which is a beveling process of compressing and thinning edges of a patch; and a third process 30, which is a complete cutting process of blanking a release sheet to form a handle part, wherein any one among the first to third processes is applied depending on the type of the patch, allowing different types of medical patches to be molded in a single process line.

Moreover, the first process 10, the second process 20, and the third process 30 are sequentially arranged in the single process line, wherein after supplying the medical patch fabric sheet to the sequentially arranged single process line, the patch fabric sheet passes through the first to third processes in sequence, and one of the first to third processes is selectively performed depending on the type of the patch to complete the patch.

Furthermore, referring to FIGS. 1 to 2, the single process line includes:

- a fabric sheet supply unit 100, which supplies a fabric sheet 90 on which a release sheet is adhered while unrolling the fabric sheet;

an eye-mark recognition unit 200, which recognizes eye marks formed on the surface of the fabric sheet 90;

a molding unit 300, which heats, presses and molds the fabric sheet 90 into a predetermined shape using a press mold having a built-in heater;

a cooling unit 400, which cools the fabric sheet 90 molded in the molding unit 300;

a fabric sheet half-cutting unit 500, which forms half-cut grooves along the outer boundary of a molded part of the fabric sheet 90 in a cooled state by the cooling unit 400;

a fabric sheet retrieval unit 600, which retrieves remaining fabric sheet except for patch fabric 91 cut by the fabric sheet half-cutting unit 500;

a release sheet complete-cutting unit 650, which forms grooves along the outer boundary of a handle part on the surface of the release sheet exposed by the fabric sheet retrieval unit 600;

a protective film supply unit 700, which supplies a protective film;

a protective film half-cutting unit 800, which removes edges of the protective film; and a protective film retrieval unit 900, which retrieves remaining protective film except for the protective film cut by the protective film half-cutting unit 800.

Additionally, the eye-mark recognition unit 200 which recognizes the eye marks formed on the surface of the fabric sheet 90 corresponds to the first process, the molding unit 300 and the cooling unit 400 correspond to the second process, and the release sheet complete-cutting unit 650 corresponds to the third process.

Furthermore, depending on the selective operation of the first process 10, the second process 20, and the third process 30, the results of the first process 10 are divided into first-process non-performed products 11 and first-process performed products 12; the results of the second process 20 are divided into second-process non-performed products 21 and second-process performed products 22; and the results of the third process 30 are divided into third-process non-performed products 31 and third-process performed products 32.

Thus, according to the paths of the first to third processes, a total of eight types of patches can be produced in the single process line.

Additionally, the types of the patches produced in the single process line are manufactured as one of the first to eighth patches by performing the remaining operations excluding the first to third processes.

The first patch is manufactured without performing the eye-mark recognition unit 200, without performing the molding unit 300 and the cooling unit 400, and without performing the release sheet complete-cutting unit 650.

Furthermore, the second patch is manufactured without performing the eye-mark recognition unit 200, without performing the molding unit 300 and the cooling unit 400, but by performing the release sheet complete-cutting unit 650.

The third patch is manufactured without performing the eye-mark recognition unit 200, by performing the molding unit 300 and the cooling unit 400, and without performing the release sheet complete-cutting unit 650.

The fourth patch is manufactured without performing the eye-mark recognition unit 200, by performing the molding unit 300 and the cooling unit 400, and by performing the release sheet complete-cutting unit 650.

The fifth patch is manufactured by performing the eye-mark recognition unit 200, without performing the molding unit 300 and the cooling unit 400, and without performing the release sheet complete-cutting unit 650.

The sixth patch is manufactured by performing the eye-mark recognition unit 200, without performing the molding unit 300 and the cooling unit 400, and by performing the release sheet complete-cutting unit 650.

The seventh patch is manufactured by performing the eye-mark recognition unit 200, by performing the molding unit 300 and the cooling unit 400, and without performing the release sheet complete-cutting unit 650.

The eighth patch is manufactured by performing the eye-mark recognition unit 200, by performing the molding unit 300 and the cooling unit 400, and by performing the release sheet complete-cutting unit 650.

Additionally, referring to FIGS. 2 to 4, when the first process is performed, on the surface of the fabric sheet, eye marks are printed and sets 333 with a plurality of characters are printed based on the eye marks.

The sets and the eye marks are alternately arranged, and a total of n eye marks are printed, and $i^{th}$ mark (where i represents the index of the eye mark: i=1, 2, 3, . . . , p−1, p, p+1, . . . , n−1, n) is printed.

Similarly, a total of n sets are printed, and $j^{th}$ set (where j represents the index of the eye mark: j=1, 2, 3, . . . , p−1, p, p+1, . . . , n−1, n) is printed, and the printing order alternates as $1^{st}$ mark, $1^{st}$ set, $2^{nd}$ mark, $2^{nd}$ set, . . . , $p^{th}$ mark, $p^{th}$ set, . . . , $n^{th}$ mark, and $n^{th}$ set.

Additionally, $p^{th}$ mark is printed before $p^{th}$ set, the $p^{th}$ set contains m characters, and the character is represented as $k^{th}$ character (where k represents the index of the character: k=1, 2, 3, . . . , q−1, q, q+1, . . . , m−1, m). All sets, including the $p^{th}$ set, contain m characters.

In addition, at the position of the $p^{th}$ mark, each position of the m characters printed on the $p^{th}$ set are arranged at different positions based on the $p^{th}$ mark.

Additionally, at the position of the $p-1^{th}$ mark, each position of the m characters printed on the $p-1^{th}$ set are arranged at different positions based on the $p-1^{th}$ mark, and at the position of the $p+1^{th}$ mark, each position of the m characters printed on the $p+1^{th}$ set are arranged at different positions based on the $p+1^{th}$ mark.

Furthermore, a vector value (p−1 #q) obtained from a coordinate value (X_p−1$q, Y_p−1$q) ranging from the center of the $p-1^{th}$ mark to the center of $q^{th}$ character printed on the $p-1^{th}$ set, a vector value (p #q) obtained from a coordinate value (X_p$q, Y_p$q) ranging from the center of the $p^{th}$ mark to the center of $q^{th}$ character printed on the $p^{th}$ set, and a vector value (p+1 #q) obtained from a coordinate value (X_p+1$q, Y_p+1$q) ranging from the center of the $p+1^{th}$ mark to the center of $q^{th}$ character printed on the $p+1^{th}$ set are the same.

Furthermore, since the vector values i #q obtained from the coordinate value ranging from the center of all marks to the center of $q^{th}$ character printed immediately after the corresponding mark are the same (where i is the index of the eye mark: i=1, 2, 3, . . . , p−1, p, p+1, . . . , n−1, n), and the values are as follows: 1 #q=2 #q=3 #q=p #q=n−1 #q=n #q.

Furthermore, since the vector values obtained from the coordinate value ranging from the center of all marks to the center of the third character printed immediately after the corresponding mark are the same, and the values are as follows: 1 #3=2 #3=3 #3=p #3=n−1 #3=n #3.

In other words, the distance between the eye mark and the characters in one set is always uniformly maintained.

For convenience in the present invention, the coordinate value ranging from the center of the $p^{th}$ mark to the center of $q^{th}$ character printed on the $p^{th}$ set is expressed as (X_p$q, Y_p$q), and the vector value derived from the corresponding coordinate value is expressed as p #q.

Although exemplary embodiments of the present invention have been disclosed for illustrative purposes, it will be appreciated that the present invention is not limited thereto, and those skilled in the art will appreciate that various modifications, additions and substitutions are possible, without departing from the scope and spirit of the invention.

Accordingly, any and all modifications, variations or equivalent arrangements should be considered to be within the scope of the invention, and the detailed scope of the invention will be disclosed by the accompanying claims.

What is claimed is:

1. A method for molding medical patches using a medical patch molding apparatus comprising:

a first process, which is an eye-mark recognition process for recognizing eye marks formed on the surface of a fabric sheet;

a second process, which is a beveling process of compressing and thinning edges of a patch; and a third process, which is a complete cutting process of blanking a release sheet to form a handle part, wherein any one among the first to third processes is applied depending on a type of the patch, allowing different types of medical patches to be molded in a single process line-, wherein the first process, the second process, and the third process are sequentially arranged in the single process line, wherein after supplying the fabric sheet to the sequentially arranged single process line, the fabric sheet passes through the first to third processes in sequence, wherein one of the first to third processes is selectively performed depending on the type of the patch to complete the patch, wherein the single process line includes:

a fabric sheet supply unit, which supplies the fabric sheet on which the release sheet is adhered while unrolling the fabric sheet;

an eye-mark recognition unit, which recognizes the eye marks formed on the surface of the fabric sheet;

a molding unit, which heats, presses and molds the fabric sheet into a predetermined shape using a press mold having a built-in heater;

a cooling unit, which cools the fabric sheet molded in the molding unit;

a fabric sheet half-cutting unit, which forms half-cut grooves along an outer boundary of a molded part of the fabric sheet in a cooled state by the cooling unit;

a fabric sheet retrieval unit, which retrieves a remaining fabric sheet except for a patch fabric cut by the fabric sheet half-cutting unit;

a release sheet complete-cutting unit, which forms grooves along an outer boundary of the handle part on a surface of the release sheet exposed by the fabric sheet retrieval unit;

a protective film supply unit, which supplies a protective film;

a protective film half-cutting unit, which removes edges of the protective film; and a protective film retrieval unit, which retrieves a remaining protective film except for the protective film cut by the protective film half-cutting unit, wherein the eye-mark recognition unit corresponds to the first process, the molding unit and the cooling unit correspond to the second process, and the release sheet complete-cutting unit corresponds to the third process, wherein when the first process is performed, on the surface of the fabric sheet, the eye marks are printed and sets with a plurality of characters are printed based on the eye marks, wherein the sets and the eye marks are alternately arranged, a total of n eye marks are printed, and an $i^{th}$ eye mark is printed, where i represents an index of the eye marks and i=1, 2, 3, . . . , p−1, p, p+1, . . . , n−1, n, wherein a total of n sets are printed, and a $i^{th}$ set is printed, where i represents an index of the sets and i=1, 2, 3, . . . , p−1, p, p+1 . . . , n−1, n, wherein a printing order of the eye marks and the sets alternates as a 1st eye mark, a 1st set, a 2nd eye mark, a 2nd set, . . . , a $p^{th}$ eye mark, a $p^{th}$ set, . . . , an $n^{th}$ eye mark, and an $n^{th}$ set, wherein the $p^{th}$ eye mark is printed before the $p^{th}$ set, the $p^{th}$ set contains m characters, and each character among the m characters is represented as a kth character, where k represents an index of the m characters and k=1, 2, 3, . . . , q−1, q, q+1, . . . , m−1, m, wherein all of the sets, including the $p^{th}$ set, contain m characters, wherein each position of the m characters printed on the $p^{th}$ set is arranged at a different position based on a position of the $p^{th}$ eye mark, each position of the m characters printed on a $p-1^{th}$ set is arranged at a different position based on a position of a $p-1^{th}$ eye mark, and each position of the m characters printed on a $p+1^{th}$ set is arranged at a different position based on a position of a $p+1^{th}$ eye mark wherein a first vector value obtained from a first coordinate value ranging from a center of the $p-1^{th}$ eye mark to a center of a $q^{th}$ character printed on the $p-1^{th}$ set, a second vector value obtained from a second coordinate value ranging from a center of the $p^{th}$ eye mark to a center of a $q^{th}$ character printed on the $p^{th}$ set, and a third vector value obtained from a third coordinate value ranging from a center of the p+1th eye mark to a center of a $q^{th}$ character printed on the $p+1^{th}$ set are the same, wherein vector values obtained from coordinate values ranging from a center of each eye mark among all of the n eye marks to a center of a $q^{th}$ character printed on a set printed immediately after each eye mark are the same, wherein a distance between each eye mark among the n eye marks and the m characters in the set printed immediately after each eye mark is uniformly maintained, and wherein the eye marks recognized in the first process enable the molding of the fabric sheet by the molding unit and the forming of the half-cut grooves by the fabric sheet half-cutting unit to be accurately performed at a correct position on the fabric sheet on which the sets are printed.

2. The method for molding medical patches according to claim 1, wherein depending on the selective operation of the first process, the second process, and the third process, the results of the first process are divided into first-process non-performed products and first-process performed products, the results of the second process are divided into second-process non-performed products and second-process performed products, and the results of the third process are divided into third-process non-performed products and third-process performed products, and wherein according to the paths of the first to third processes, a total of eight types of patches can be produced in the single process line.

3. The method for molding medical patches according to claim 2, wherein the types of the patches produced in the single process line are one of:

a first patch manufactured without performing the eye-mark recognition unit, without performing the molding unit and the cooling unit, and without performing the release sheet complete-cutting unit;

a second patch manufactured without performing the eye-mark recognition unit, without performing the molding unit and the cooling unit, but by performing the release sheet complete-cutting unit;

a third patch manufactured without performing the eye-mark recognition unit, by performing the molding unit and the cooling unit, and without performing the release sheet complete-cutting unit;

a fourth patch manufactured without performing the eye-mark recognition unit, by performing the molding unit and the cooling unit, and by performing the release sheet complete-cutting unit;

a fifth patch manufactured by performing the eye-mark recognition unit, without performing the molding unit and the cooling unit, and without performing the release sheet complete-cutting unit;

a sixth patch manufactured by performing the eye-mark recognition unit, without performing the molding unit and the cooling unit, and by performing the release sheet complete-cutting unit;

a seventh patch manufactured by performing the eye-mark recognition unit, by performing the molding unit and the cooling unit, and without performing the release sheet complete-cutting unit; and an eighth patch manufactured by performing the eye-mark recognition unit, by performing the molding unit and the cooling unit, and by performing the release sheet complete-cutting unit.

* * * * *